US009232788B2

(12) United States Patent
Poss et al.

(10) Patent No.: US 9,232,788 B2
(45) Date of Patent: Jan. 12, 2016

(54) FUMIGATION METHODS

(71) Applicant: Honeywell International Inc., Morristown, NJ (US)

(72) Inventors: Andrew J. Poss, Kenmore, NY (US); Rajiv R. Singh, Getzville, NY (US); David Nalewajek, West Seneca, NY (US); Cheryl L. Cantlon, Clarence Center, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 13/651,565

(22) Filed: Oct. 15, 2012

(65) Prior Publication Data

US 2013/0109570 A1  May 2, 2013

Related U.S. Application Data

(60) Provisional application No. 61/554,623, filed on Nov. 2, 2011.

(51) Int. Cl.
 *A01N 29/00* (2006.01)
 *A01N 29/02* (2006.01)
 *A61K 31/02* (2006.01)

(52) U.S. Cl.
 CPC ..................... *A01N 29/02* (2013.01)

(58) Field of Classification Search
 None
 See application file for complete search history.

(56) References Cited

U.S. PATENT DOCUMENTS

| | | | |
|---|---|---|---|
| 3,321,517 A | 5/1967 | Selman | |
| 3,878,257 A | 4/1975 | Bruce, Jr. | |
| 4,997,855 A | 3/1991 | Peake | |
| 5,610,128 A * | 3/1997 | Zyhowski et al. | 510/288 |
| 6,103,844 A | 8/2000 | Brothers | |
| 6,706,344 B1 | 3/2004 | Harlowe, Jr. et al. | |
| 7,544,306 B2 * | 6/2009 | Poss et al. | 252/67 |
| 7,695,635 B2 * | 4/2010 | Singh et al. | 252/67 |
| 8,637,443 B2 * | 1/2014 | Basu et al. | 510/400 |
| 8,668,791 B2 * | 3/2014 | Leck et al. | 149/67 |
| 2010/0081570 A1 | 4/2010 | Poss et al. | |
| 2010/0186432 A1 | 7/2010 | Perti et al. | |

FOREIGN PATENT DOCUMENTS

| | | |
|---|---|---|
| EP | 1084093 B1 | 8/2004 |
| WO | 0151097 A2 | 7/2001 |
| WO | WO 0151097 * | 7/2001 |
| WO | 2008101054 A1 | 8/2008 |
| WO | WO 2008101054 * | 8/2008 |
| WO | 2011133292 A2 | 10/2011 |

OTHER PUBLICATIONS

PCT ISR & Written Opinion issued in PCT/US2012/062350 dated Mar. 4, 2013.
Ohr et al., Methyl Iodide, an Ozone-Safe Alternative to Methyl Bromide as a Soil Fumigant, Plant Disease, Jul. 1996, pp. 731-735.
Recent Nematicides, pp. 1377-1385, author unknown, dated prior to filed of present application.
"Acute Exposure Guideline Levels" (AEGLs)—Hexafluoropropylene (CAS Reg. No. 116-15-4) Interim 1: Nov. 2007; 54 pages.
"Consideration of Hydrofluoroolefins (HFOs) as potential candidate medical propellants" A. A. Lindley & T. J. Noakes Mexichem Fluor Apr. 2010—21 pages.
"A Series of Pesticides Based on Fluorine Monomer" Technology Research Institute of Shanghai Huayi Group, Shanghai 200241, China Shi Xian-feng, Liu Bin, Liao Ben-ren vol. 50, No. 11, Nov. 2011; (in Chinese language and Certified English Translation) X.
Information from Stn International regarding publication date for Document No. 195:21902 4 pages.

* cited by examiner

*Primary Examiner* — Alton Pryor
(74) *Attorney, Agent, or Firm* — Colleen D. Szuch

(57) ABSTRACT

Fumigant compositions including hexafluoropropene or 1,1,3,3,3-pentafluoropropene, and methods of preparing such compositions, are provided herein. The fumigant compositions may be suitable for use as soil fumigant compositions and structural fumigant compositions against a variety of undesirable species such as weeds, nematodes, pathogens, animals and insects. The fumigant compositions also have low toxicity and low Global Warming Potential.

19 Claims, 1 Drawing Sheet

__US 9,232,788 B2__

FUMIGATION METHODS

RELATED APPLICATIONS

This application claims the benefit of U.S. Provisional Application Ser. No. 61/554,623 filed Nov. 2, 2011 entitled "Fumigation Compositions and Methods," which application is incorporated by reference herein.

FIELD OF THE INVENTION

The present technology relates to compositions and formulations for soil and structural fumigation, methods of preparing such formulations, and methods of fumigating soil and structures with such compositions.

DESCRIPTION OF RELATED ART

Historically, methyl bromide ($CH_3Br$) has been the most widely used and most universal fumigant in the world. It is known for being extremely effective as a herbicide, nematocide, insecticide and fungicide. Consequently, it has been used extensively for soil fumigation, as a commodity quarantine treatment for exports and imports, to control a variety of pests on numerous crops, and as a structural fumigant applied to building surfaces. However, methyl bromide contributes to the depletion of the ozone layer in the stratosphere. In accord with the Montreal Protocol, the import and manufacture of methyl bromide in the United States and other developed countries was banned in 2005.

Various compounds such as 1,3-dichloropropene, chloropicrin, metham sodium, and methyl iodide have been identified as alternatives to methyl bromide. These alternatives are commonly applied as mixtures of two or more of the individual compounds in order to attempt to produce a broader spectrum product similar to methyl bromide.

As new fumigants are introduced, their global warming potential (GWP) is also being scrutinized. GWP is a relative measure of how much heat a greenhouse gas traps in the atmosphere. It compares the amount of heat trapped by a certain mass of the gas in question to the amount of heat trapped by a similar mass of carbon dioxide. GWP is calculated over a specific time interval, commonly 20, 100 or 500 years. GWP is expressed as a factor of carbon dioxide (whose GMP is standardized to 1). For example, the 20 year GWP of methane is 56, which means if the same weights of methane and carbon dioxide were introduced into the atmosphere, that methane will trap 56 times more heat than the carbon dioxide over the next 20 years.

SUMMARY OF THE INVENTION

Fumigant compositions and methods of preparing such compositions are provided herein. The fumigant compositions may be suitable for use as soil fumigant compositions and structural fumigant compositions.

DETAILED DESCRIPTION

Figure 1:
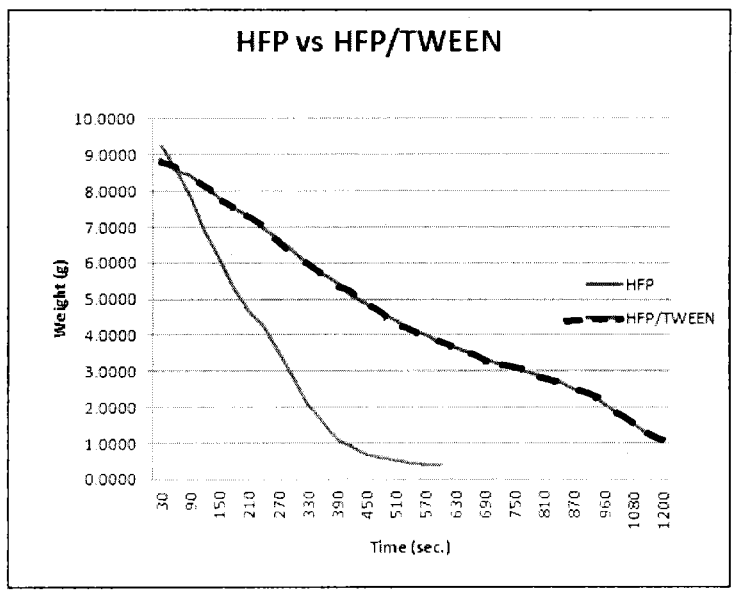
FIG. 1 is a graphical representation of experimental data.

Embodiments of the present invention include fumigant compositions comprising an alkylene fluorocarbon including at least one $C=CF_2$ group. The fluorocarbon may also have a low toxicity and a low GWP. For example, the fluorocarbon may have a GWP of less than 1, more particularly, less than 0.5.

These fumigant compositions may be used against a variety of different undesirable species, such as weeds, nematodes or pathogens. In some embodiments, these fumigant compositions may be used against a variety of different insects, including but not limited to termites, cockroaches, mites and bed bugs. In some embodiments, these fumigant compositions may be used against animals such as gophers, mice, moles, rats and other rodent pests.

These fumigant compositions may be used in a variety of different treatment zones. Broadly, a treatment zone is a surface, space or other volume that contains undesirable species. In some embodiments, for example, the treatment zone may be a building such as a warehouse or store or a vehicle such as a tractor trailer or a rail car.

Fumigant Composition

The fumigant composition includes an alkylene fluorocarbon including at least one $C=CF_2$ group. In some embodiments, the alkylene fluorocarbon has a three carbon backbone. In some instances, smaller alkylene fluorocarbons have been found to polymerize too quickly to be useful while larger alkylene fluorocarbons have been found to be less effective.

In some embodiments, the fumigant composition comprises or consists essentially of hexafluoropropene ("HFP"), or 1,1,3,3,3-pentafluoropropene ("1225zc"), which have the following structures, respectively:

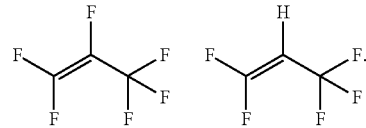

Hexafluoropropene has a lifetime of only 5.8 days which translates into a GWP of about 0.25. 1,1,3,3,3-Pentafluoropropene also contains a highly reactive carbon-carbon double bond and therefore has a GWP of less than 1. Both compounds also have negligible ozone depletion potential.

The fluorocarbon may be present in an initial mixture (e.g., prior to diluting into a use solution) in an amount as low as about 1 weight percent (wt. %), in an amount as low as about 30 wt. %, in an amount as low as about 40 wt. % or in an amount as low as about 50 wt. %. The fluorocarbon may be present in an initial mixture, prior to dilution, in an amount as high as about 75 wt. %, in an amount as high as about 85 wt. %, in an amount as high as about 95 wt. % or in an amount as high as about 99 wt. %. The fluorocarbon may further be present within any range deliminated by any pair of the foregoing values set forth in this paragraph. In some examples, the fluorocarbon may have a boiling point of from about −50° C. to about 50° C.

In addition to the fluorocarbon, the fumigant compositions may also include at least one additional active ingredient. Suitable actives for the fumigant compositions include, but are not limited to, methyl iodide, chloropicrin, acrolein, 1,3-dichloropropene, dimethyl disulfide, furfural, metham sodium and propylene oxide. In certain embodiments, both HFP and 1225zc may be used with or without additional actives.

Methyl iodide can be present in the initial mixture in any suitable amount, including for example, in an amount as low as about 5 wt. %, in an amount as low as about 15 wt. % or in an amount as low as about 25 wt. %. Methyl iodide can be present in the initial mixture in an amount as high as about 50 wt. %, in an amount as high as about 60 wt. % or in an amount as high as about 70 wt. %. Methyl iodide may further be present within any range deliminated by any pair of the foregoing values set forth in this paragraph.

The fumigant compositions according to embodiments of the present invention may further include various additives. In one embodiment, the fumigant composition may include at least one surfactant. Suitable surfactants for use in fumigant compositions can be ionic surfactants or non-ionic surfactants. Non-ionic surfactants that can be suitable in fumigant compositions include, but are not limited to: Arkopal™ (a nonylphenol ethoxylate), Cetomacrogol™ 1000 (a polyethylene glycol), cetostearyl alcohol, cetyl alcohol, cocamide DEA, cocamide MEA, decyl glucoside, glyceryl laurate, lauryl glucoside, narrow range ethoxylates, nonoxynols, NP-40, octaethylene glycol monododecyl ether, octyl glucoside, oleyl alcohol, pentaethylene glycol, monododecyl ether, poloxamer, polyglycerol polyricinoleate, polysorbate, polysorbate 20, polysorbate 40, polysorbate 60, polysorbate 80, sorbitan monostearate, sorbitan tristearate, stearyl alcohol, Triton™ X-100 (polyethylene oxide chain with an aromatic hydrocarbon group), and Tween™ 80 (a polysorbate). In one specific example, the surfactant can be a polysorbate, which can be polysorbate 20, polysorbate 40, polysorbate 60 or polysorbate 80.

The surfactant can be included in an amount that is as low as about 0.1 wt. %, in an amount as low as about 3 wt. % or in an amount as low as about 5 wt. %. The surfactant can be included in an amount that is as high as about 15 wt. %, in an amount as high as about 30 wt. % or in an amount as high as about 50 wt. %. The surfactant may further be present within any range deliminated by any pair of the foregoing values set forth in this paragraph.

In some embodiments, the HFP or 1225zc can be diluted with a suitable carrier solvent that can include at least one C3-C4 hydrofluorocarbon olefin or at least one hydrochlorofluorocarbon olefin which preferably have a combination of desirable environmental and functional properties. For example, environmentally, the carrier solvents can have an ozone depletion potential (ODP) that is zero or about zero. Carrier solvents may also have a low global warming potential, which can preferably be less than or equal to about 10 relative to CO2. Functionally, carrier solvents are preferably volatile, non-toxic, and non-flammable. Co-solvents for use with this technology include mixtures of tetrafluoropropenes, hexafluorobutenes and chlorotrifluoropropenes. The carrier solvents can include an azeotropic or azeotrope-like mixture of the at least one C3-C4 hydrofluorocarbon olefin or the at least one hydrochlorofluorocarbon olefin with an organic compound.

The solvent can be included in an amount that is as low as about 1 wt. %. The solvent can be included in an amount as high as about 5 wt. %, in an amount as high as about 50 wt. % or in an amount as high as about 99 wt. %. The solvent may further be present within any range deliminated by any pair of the foregoing values set forth in this paragraph.

For safety purposes, the fumigant composition may include an odorant such as banana oil or chloropicrin since certain fluorocarbons including HFP and 1225zc have no detectable odor.

Application Techniques

The fumigant composition may be applied to soil or structures as part of an aqueous solution or dispersion. The fumigant composition may by applied by a number of different procedures that are currently employed for soil and structural treatments.

In some embodiments, soil fumigant may utilize either shank injection or drip irrigation. In shank injection fumigant, the chemical fumigant is applied to the soil by injection through hollow shanks that are pulled through the soil, either at shallow depths followed by plastic mulch film application, or at deep depths followed by soil compaction.

Application of the chemical fumigant via drip irrigation involves introducing and dispersing the chemical fumigant through an existing irrigation system. This provides an advantage of minimizing potential exposure to workers, as this can be done without workers in the field.

The irrigation system may include one or more dripperlines having a plurality of emitters therein. The emitters, also known as drippers, can be of any suitable type, including for example pre-punched holes or porous pipe. The emitters can be formed as an integral part of a dripperline, or can be separately produced and installed on or in the one or more dripperlines. The emitters can be spaced apart at any suitable distance, including for example, from about 8 inches apart to about 24 inches apart (from 200 mm to 600 mm apart).

In some examples, the one or more dripperlines can be placed below the soil that is to be fumigated. Application of the fumigant composition to the soil can include providing pressure to cause the fumigant composition to flow through the one or more dripperlines and exit the one or more dripperlines through the plurality of emitters to contact and flow into the soil. Alternatively, the fumigants may be applied to the soil by tractor mounted injectors, manually in canisters or as a gas through lay-flat tubing.

The behavior of the fumigant compositions in use is a function of their water solubility, volatility, hydrolysis and degradation rates, and their sorption to soil organic matter and clay. The physical and chemical properties of the fumigants, such as: water solubility, vapor pressure, boiling point, Henry's constant and half life in soil, are good indicators of how each chemical will behave in the soil-air-water system. The efficacy of a fumigant correlates to its distribution patterns in soils and applications that maximize concentrations in the pest-infested zone give better control.

For structural fumigation the chemicals may be heated to a gas before introduction within a building, chamber, vehicle or other space or structure. The space or structure is preferably sealed with a tarpaulin, fumigant tape or gas impermeable sheeting. In some embodiments, structural fumigant, particularly for rodents, involves sealing the structure as tightly as possible. In some embodiments, a 2 to 4 mil polyethylene cover may be used to wrap the structure before providing the fumigant composition. In some embodiments, the structure may subsequently be aerated to remove the fumigant composition.

Stacked commodities may be treated by draping the commodities with a gas-impermeable tarp or sheet that can be sealed to an impermeable surface (such as a concrete floor) using, for example, sand-filled tubes. After sufficient fumigant composition has been released under the tarp, the space may be aerated to remove remaining fumigant composition.

The fumigant compositions can be prepared by combining the at least one fluorocarbon, the optional active, at least one surfactant and water to form a fumigant composition. The fumigant composition can be a solution or a homogeneous mixture, which can be formed by mixing the combined initial mixture, the at least one surfactant and the water under suitable conditions. In one example, the fumigant compositions can be formed by mixing the components at a temperature at or below about 60° F. (15.5° C.).

Example 1

Fumigant tests on seeds of the broadleaf species *Abutilon theophrasti* Medik. and the grass weed species *Lolium multiflorum* Lam. demonstrate that both HFP and 1125c completely prevented seed germination. Since weeds are generally more resistant to fumigant than most nematodes or soil-borne plant-pathogenic fungi (See Ohr et al., "Methyl Iodide, an Ozone-Safe Alternative to Methyl Bromide and a Soil Fumigant," Plant Disease, July 1996, pp. 731-735; See also Zhang et al., "Effect of Soil Physical Factors on Methyl Iodide and Methyl Bromide", Pestic. Sci. 1998, pp. 53, 71-79), this result indicates that either of these chemicals can be employed as a fumigant for the effective control of plant pathogens, nematodes, bacteria and weeds.

In particular, in 440 mL pressure vessels, fourteen seeds of *Abutilon theophrasti* Medik. and fifteen seeds of *Lolium multiflorum* Lam. were thoroughly mixed with 50 mL (approximately 30 grams) of soil and 6 mL of water. The filled vessels were kept at room temperature for 20-24 hr to allow the seeds to imbibe water before treatment. The vessels were sealed and evacuated, and then 80 ml, 160 ml and 440 ml respectively of gaseous 1225zc was added. The vessels were thoroughly mixed and placed horizontally on the laboratory bench at ambient temperature for two days. The contents of each bottle were transferred to a plastic sterile Petri dish containing 7 mL of water. The Petri dishes were sealed with parafilm and incubated in the laboratory at ambient temperature. After 10 days, the number of germinated seeds was counted. As shown in Table 1 below, none of the seeds treated with 1225zc showed any signs of germination.

TABLE 1

| | Seeds Germinated | |
|---|---|---|
| Fumigant | *Abutilon theophrastic* Medik. | *Loliium multiflorum* Lam. |
| Control | 14 | 15 |
| 80 ml 1225zc | 0 | 0 |
| 160 ml 1225zc | 0 | 0 |
| 440 ml 1225zc | 0 | 0 |

Example 2

The same experiment was performed as described in Example 1 except that hexafluoropropene (HFP) was used as the active fumigant composition. As shown in Table 2, no germination occurred under any of the experimental concentrations.

TABLE 2

| | Seeds Germinated | |
|---|---|---|
| Fumigant | *Abutilon theophrastic* Medik. | *Loliium multiflorum* Lam. |
| Blank | 14 | 15 |
| 80 ml HFP | 0 | 0 |
| 160 ml HFP | 0 | 0 |
| 440 ml HFP | 0 | 0 |

The eradication of a broadleaf weed species (*Abutilon theophrastic* Medik.) and a grass weed species (*Lolium multiflorum* Lam.) indicates that HFP and 1225zc are suitable as general purpose fumigant compositions to eradicate weeds, nematodes and soil-borne plant-pathogenic fungi.

Example Three

Experimentation was carried out to determine the volatility of aqueous fumigant compositions, both with and without inclusion of a surfactant. In each case, the fluorocarbon was placed in a chilled 500 ml Fischer Porter tube that was equipped with a vent to remove any gases. The vessel was cooled to 0° C. and was charged with varying amounts of water, fluorocarbon and surfactant. The temperature was equilibrated to 20° C. and the reactor was placed on a balance. The vent tube was opened and the weight loss was recorded every 30 seconds.

In analyzing the effects of adding surfactant to an aqueous solution of HFP, 10.11 grams of HFP was added to 39.71 grams of water. In a separate experiment, 9.83 grams of HFP and 4.03 grams of Tween™ 80 were added to 40.08 grams of water. FIG. 1 provides a graphical representation of the numerical data comparing the volatility of an aqueous solution of HFP, both with and without inclusion of the Tween™ 80 nonionic surfactant. As can be seen, inclusion of the surfactant provides for longer retention of the HFP in solution.

Figure 2:
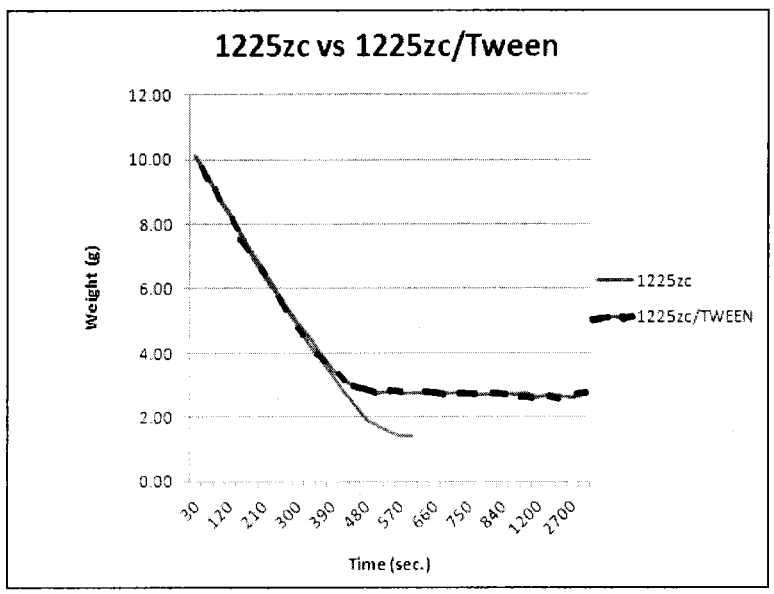
FIG. 2 is a graphical representation of experimental data.

In analyzing the effects of adding surfactant to an aqueous solution of 1225zc, 10.78 grams of 1225zc were added to 39.69 grams of water. In a separate experiment, 10.70 grams of 1225zc and 4.08 grams of Tween™ 80 were added to 40.15 grams of water. FIG. 2 provides a graphical representation of the numerical data comparing the volatility of an aqueous solution of 1225zc, both with and without inclusion of the Tween™ 80 nonionic surfactant. As can be seen, inclusion of the surfactant provides for longer retention of the 1225zc in solution.

The invention claimed is:

1. A method of eradicating undesirable species from soil, the method comprising:
    contacting the soil with a fumigant composition comprising: (i) one or more active compounds and (ii) optionally carrier for said one or more active compounds, said active compounds comprising at least or about 30% by weight of hexafluoropropene based on the weight of the active compounds, wherein the hexafluoropropene in amount effective to control the undesirable species.

2. The method of claim 1, wherein the undesirable species include one or more of weeds, nematodes or pathogens.

3. The method of claim 1, wherein the soil is in a field.

4. The method of claim 1, wherein said contacting soil comprises contacting soil via drip irrigation.

5. The method of claim 1, wherein contacting soil comprises contacting soil via shank injection.

6. The method of claim 1, wherein the fumigant composition is in gaseous form.

7. The method of claim 1, wherein the fumigant composition is in aqueous form.

8. The method of claim 1, wherein the one or more active compounds further comprise at least one of methyl iodide, chloropicrin, acrolein, 1,3-dichloropropene, dimethyl disulfide, furfural, propylene oxide or metham sodium.

9. The method of claim 1, wherein the fumigant composition further comprises at least one surfactant.

10. The method of claim 1, wherein the fumigant composition further comprises at least one odorant.

11. The method of claim 1 wherein said fumigant composition consists essentially of hexafluoropropene, methyl iodide and a surfactant.

12. The method of claim 1 wherein said fumigant composition comprises carrier.

13. The method of claim 12 wherein said carrier is a carrier solvent.

14. The method of claim 13 wherein said carrier solvent comprises at least one three carbon hydrofluorocarbon olefin.

15. The method of claim 14 wherein said at least one three carbon hydrofluorocarbon olefin is selected from the group consisting of tetrafluoropropenes, hexafluorobutenes and chlorotrifluoropropenes.

16. The method of claim 13 wherein said carrier solvent is present in the fumigant composition in an amount of from about 1% to about 99% by weight of the fumigant composition.

17. The method of claim 1 wherein said hexafluoropropene is in an amount of at least or about 40% by weight based on the weight of the active compounds.

18. The method of claim 1 wherein said hexafluoropropene is in an amount of at least or about 50% by weight based on the weight of the active compounds.

19. The method of claim 1 wherein said hexafluoropropene is in an amount of up to about 99% by weight based on the weight of the active compounds.

* * * * *